United States Patent [19]

Mich et al.

[11] 4,315,933
[45] Feb. 16, 1982

[54] ANTIBACTERIAL AMIDE COMPOUNDS AND PHARMACEUTICAL COMPOSITIONS CONTAINING THE SAME

[75] Inventors: Thomas F. Mich; Theodore H. Haskell, both of Ann Arbor; Marland P. Hutt, Jr., Saline, all of Mich.

[73] Assignee: Warner-Lambert Company, Morris Plains, N.J.

[21] Appl. No.: 190,154

[22] Filed: Sep. 24, 1980

[51] Int. Cl.$^3$ .................. A61K 31/505; C07D 499/70
[52] U.S. Cl. ............................... 424/251; 260/239.1; 544/319
[58] Field of Search ...................... 260/239.1; 424/251

[56] References Cited

U.S. PATENT DOCUMENTS 4,218,451  8/1980  Feyen et al. .................. 424/250
4,267,180  5/1981  Haskell et al. ................ 424/251

Primary Examiner—Natalie Trousof
Assistant Examiner—Vera C. Clarke
Attorney, Agent, or Firm—Stephen Raines

[57] ABSTRACT

Novel organic amide compounds which are N-[2-(acylaminophenyl)-4-hydroxy-5-pyrimidinylcarbonyl]-penicillin compounds having broad spectrum antibacterial utility are provided by (a) reacting the free amino acid of the appropriate penicillin or the acid salt or silylated derivative or complex thereof with a reactive derivative of the corresponding N-2-(acylaminophenyl)-4-hydroxy-5-pyrimidine carboxylic acid or (b) reacting the free amino acid 6-aminopenicillanic acid or a related compound or the acid salt or silylated derivative thereof with a reactive derivative of the corresponding D-N-[2-(acylaminophenyl)-4-hydroxy-5-pyrimidinylcarbonyl]-2-substituted glycine. Pharmaceutical compositions containing said compounds and methods for treating infections using said compositions are also disclosed.

12 Claims, No Drawings

ANTIBACTERIAL AMIDE COMPOUNDS AND PHARMACEUTICAL COMPOSITIONS CONTAINING THE SAME

SUMMARY AND DETAILED DESCRIPTION

The present invention relates to novel chemical compounds that are useful as pharmacological agents and to methods for their production. More particularly, the invention relates to novel organic amide compounds having the formula

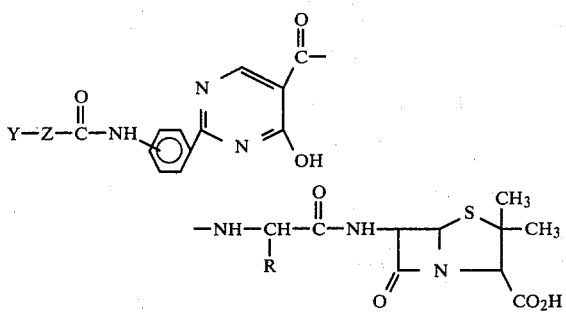

and pharmaceutically acceptable salts thereof; wherein Z is a single bond and Y is lower alkyl, dichloromethyl, benzyl, $CF_{3'}$, lower alkyl amino, lower alkyl carbonyl, lower alkoxy carbonyl, benzyloxy and lower alkoxy, where Z is a methylene group and Y is cyano, lower alkoxy, tetrazolyl or $R^1 CH_2S$ where $R^1$ is $CF_3$ or CN and R is phenyl, 4-hydroxyphenyl, 2-thienyl or cyclohexa-1,4-dien-1-yl The preferred compounds are those wherein

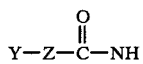

is in the p position and Z is a single bond, Y is $CF_3$ or lower alkylamino and R is 4-hydroxyphenyl Lower alkyl is defined as a hydrocarbon fragment of from one to six carbon atoms.

In accordance with the invention the foregoing amide compounds having the formula

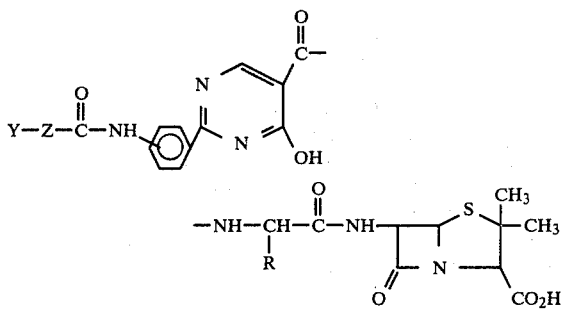

and pharmaceutically acceptable salts thereof wherein Z, Y and R are as previously defined are produced by reacting a compound of the formula

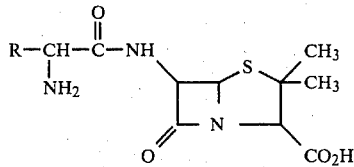

or the basic salt, silylated derivative (preferably the disilylated) or complex (preferably the dimethylsulfoxide) thereof wherein R is as previously defined, with a reactive derivative of a 4-hydroxy-5-pyrimidine carboxylic acid compound having the formula

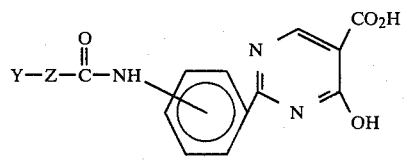

or its acid addition salt, where Z and Y all have the aforementioned significance.

Some examples of reactive derivatives of the 2-(substituted)-4-hydroxy-5-pyrimidine carboxylic acid compound suitable for the reaction are the acid halides (especially the acid chloride), the imidazolide, mixed anhydrides (especially those formed from an alkyl chloroformate such as methyl, ethyl, and isobutyl chloroformate or pivaloyl chloride), and activated esters such as the pentachlorophenyl ester and N-hydroxysuccinimide ester.

The reactants are normally employed in approximate equimolar quantities, although an excess of either (pyrimidine acid compound or amino acid compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the penicillin compounds in the free acid or salt form, aqueous solutions may be used for acylation with an acid halide or mixed anhydride under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The reactive derivative of 2-(substituted)-4-hydroxy-5-pyrimidine carboxylic acid compounds, which are required as starting materials in the foregoing process, can be prepared according to any of a variety of methods.

A 2-(substituted)-4-hydroxy-5-pyrimidine carboxylic acid may be converted to its acid chloride utilizing thionyl chloride, its mixed anhydride utilizing ethyl chloroformate, its pentachlorphenyl ester by esterification with pentachlorophenol and its imidazolide by reacting the acid with 1,1'-carbonyl-diimidazole.

Compounds of the formula

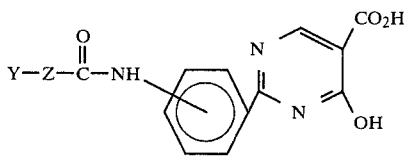

where Z and Y are as previously defined are prepared by acylation of a compound of the formula

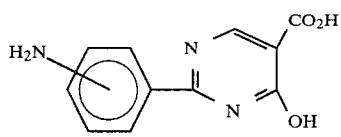

with a compound of the formula

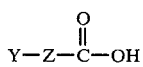

wherein Y and Z are as previously defined.

The compound of the formula

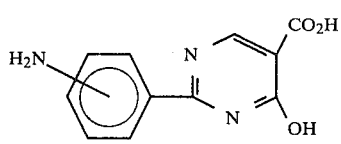

is prepared by hydrolyzing a compound of the formula

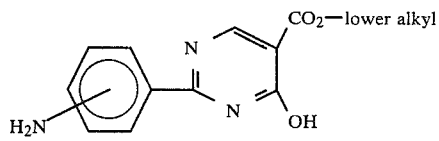

which is in turn prepared by coupling a compound of the formula

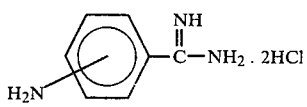

with a compound of the formula

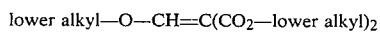

lower alkyl—O—CH=C(CO$_2$—lower alkyl)$_2$

The compound of the formula

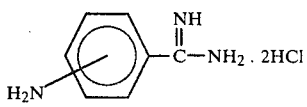

is prepared by reducing a compound of the formula

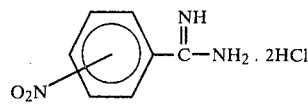

The silylated amino acid starting materials can be prepared by reacting an amino acid of the formula

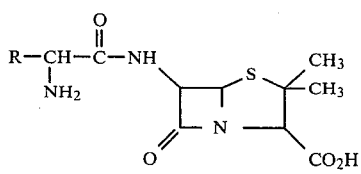

or a salt thereof wherein R is as previously defined in anhydrous form with either one or two equivalents of a tri(lower alkyl)-silyl chloride in the presence of triethylamine. The preferred silylating agents are trimethylsilyl chloride and dimethyl dichlorosilane. When two equivalents of the silylating agent are used, both the amino and the carboxyl group become silylated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formula

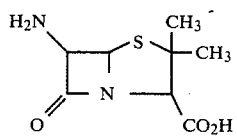

or the corresponding acid salt or silylated derivative thereof with a reactive derivative of D-N-[2-(substituted)-4-hydroxy-5-pyrimidinylcarbonyl]-2-substituted glycine having the formula

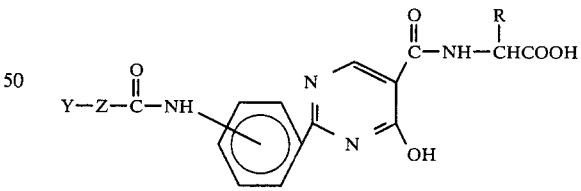

or its acid addition salts where Z, Y and R have the aforementioned significance.

Some examples of reactive derivatives of the D-N-(4-hydroxy-5-pyrimidinyl)-2-substituted glycine compounds suitable for the reaction are the acid halides, mixed anhydrides (especially those formed from an alkyl chloroformate such as ethyl chloroformate and isobutyl chloroformate), and activated esters such as the pentachlorophenyl ester and N-hydroxysuccinimide ester. Since racemization is more likely with the acid halide, the other forms are generally preferred. The reactants are normally employed in approximate equimolar quantities, although an excess of either (pyrimidine carboxylic acid compound or amino acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethyoxyethane), chlorinated hydrocarbons (such as chloroform and dichloromethane), and mixtures of these. In addition to any of these solvents, 6-aminopenicillanic acid may be reacted with an acid chloride or mixed anhydride in the free acid or salt form using aqueous solutions under normal Schotten-Baumann conditions. The duration and temperature of the reaction are not critical. Temperatures in the range from −30° to +30° C. are commonly used for reaction times ranging from a few hours up to a day or more. The product may be isolated in any suitable way as the free acid or as a salt by appropriate adjustment of the pH.

The reactive derivative of D-N-[2-(acylaminophenyl)-4-hydroxy-5-pyrimidinylcarbonyl]-2-substituted glycines or their acid-addition salts which are required as starting materials in the foregoing process can be prepared by methods illustrated in greater detail hereinafter.

D-N-[2-(acylaminophenyl)-4-hydroxy-5-pyrimidinylcarbonyl]-2-substituted glycine compounds may be prepared by reacting the corresponding reactive derivative of 2-(substituted)-4-hydroxy-5-pyrimidine carboxylic acid, such as the acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

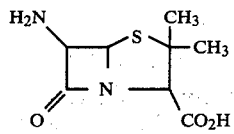

with a standard silylating agent such as chlorotrialkylsilane, hexaalkyldisilazane, etc. The preferred silylating agent is hexamethyldisilazane. Only the carboxyl group is silylated under the conditions used (e.g., 2-hour reflux in dichloromethane). After acylation, the silyl group is easily removed by treatment with water.

The free acids of the invention form salts with any of a variety of inorganic and organic bases. Pharmaceutically-acceptable salts are formed by reacting the compounds with such bases as sodium hydroxide, sodium carbonate, sodium bicarbonate, sodium 2-ethylhexanoate, potassium hydroxide, potassium carbonate, potassium 2-ethylhexanoate, calcium hydroxide, ethylamine, 2-hydroxyethylamine, and procaine. Preferred salt forms are the alkali metal salts. The salts are converted to the free acids by acidification. The free acids and their salts usually differ somewhat in solubility properties but, in general, are otherwise equivalent for the purposes of the invention.

The compounds of the invention can exist in anhydrous form, as well as in solvated, including hydrated, forms. In general, the hydrated forms and the solvated forms with pharmaceutically acceptable solvents are equivalent to the anhydrous or unsolvated forms for the purposes of the invention.

The pyrimidine segment of the compounds of this invention may be capable of undergoing keto-enol tautomerism to give 4-keto-dihydro-pyrimidines. Such a tautomer is equivalent to the 4-hydroxypyrimidines for the purposes of the inventions and are included within the above shown structures.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for certain of the preferred compounds.

Thus, the compounds of this invention and their non-toxic pharmaceutically acceptable salts are highly useful as broad spectrum antibiotics in mammals when administered in amounts ranging from about 5 mg to about 100 mg per kg of body weight per day. A preferred dosage regimen for optimum results would be from about 10 mg to about 50 mg per kg of body weight per day, and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc., the preferred route of administration is parenterally for treating systemic infections.

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg to about 1000 mg of active compound per vial. The vial may also contain other active ingredients, buffers, salts, etc. The sterile material in the vial is dissolved in water for injection at the time of use. Oral preparations would also have from about 50 mg at about 1000 mg of active compound per unit dose form.

The invention is illustrated by the following examples.

ACTIVITY TABLE

Structure: Y–Z–C(=O)–NH–[phenyl]–[pyrimidine with N, N, OH]–C(=O)–NH–CH(R)–C(=O)–NH–[β-lactam with S, CH₃, CH₃, N, CO₂H]

Minimal Inhibitory Concentration (μg/ml)

| $X-Z^a-\overset{O}{\underset{\|}{C}}-$ | $R^b$ | Pseudomonas aeruginosa #28 | Entero. cloacae | Serr. marces. | Kleb. pneu. | Staph. aureus S18713 |
|---|---|---|---|---|---|---|
| CH₃C(=O)– | HO–C₆H₄ | 1.6 | 1.6 | 200 | 12.5 | 50 |
| CF₃C(=O)– | HO–C₆H₄ | 1.6 | 6.3 | 200 | 6.3 | 200 |
| Cl₂CHC(=O)– | HO–C₆H₄ | 0.8 | 6.3 | 3.1 | 12.5 | >50 |
| CNCH₂C(=O)– | HO–C₆H₄ | 0.8 | 3.1 | 3.1 | 25 | >50 |
| CH₃OCH₂C(=O)– | C₆H₅ | 3.1 | 12.5 | 100 | 25 | 100 |
| CF₃CH₂SCH₂C(=O)– | HO–C₆H₄ | 1.6 | 12,5 | 1.6 | 25 | >50 |
| EtOC(=O)C(=O)– | HO–C₆H₄ | 6.3 | 6.3 | 200 | 50 | 50 |
| EtNHC(=O)– | HO–C₆H₄ | 0.8 | 6.3 | 3.1 | 12.5 | >50 |

[a] Y–Z group is in the 4 position.
[b] HO group is in the 4 position.

EXAMPLE 1

N-[2-[4-(Dichloroacetylamino)phenyl]-4-hydroxy-5-pyrimidinylcarbonyl]amoxicillin A suspension of 11.6 g (50 mmol) of 2-(4-aminophenyl)-4-hydroxy-5-pyrimidine carboxylic acid, 21 ml (150 mmol) of triethylamine, and 500 ml of dichloromethane is stirred at 0°–5° and 20 ml (158 mmol) of chlorotrimethylsilane is added and the mixture is stirred at room temperature for 1 hour. The resulting solution is cooled with a dry ice acetone bath and 8.4 ml (55 mmol) of dichloroacetic anhydride is added. The solution is stirred overnight while warming to room temperature. The dichloromethane is evaporated under reduced pressure and the residue is treated with water. The solid is filtered, washed with water and ether, and dried to afford 16.8 of 2-[4-(dichloroacetylamino)-phenyl]-4-hydroxy-5-pyrimidine carboxylic acid; mp>310°.

A mixture of 12.7 g (36.2 mmol) of the above pyrimidine acid, 11.73 g (72.4 mmol) of carbonyldiimidazole, and 200 ml tetrahydrofuran is stirred at 50° for 30 min and at room temperature for 1.5 hrs. The solid is filtered, washed with tetrahydrofuran and ether and dried under vacuum at 40° to afford 12.65 g of 2-[4-(dichloroacetylamine)phenyl]-4-hydroxy-5-pyrimidine carboxylic acid imidazolide.

A solution of 6.62 g (10 mmol) of amoxicillin dimethyl sulfoxide complex, 3.91 g (10 mmol) of the above imidazolide, and 75 ml of N,N-dimethylacetamide is stirred at 0°–5° and 1.4 ml (10 mmol) of triethylamine is added. The solution is stirred in the cold for 2.5 hrs and for 1 hr at room temperature. The reaction mixture is poured into 375 ml of ethyl acetate, ether is added and a gum resulted. The solvent is decanted and the gum solidified by trituration with tetrahydrofuran. The solid is filtered and dried under reduced pressure, dissolved in 150 ml of water, and filtered. The pH of the filtrate is adjusted to 6.5 with 1 N sodium hydroxide, filtered, and the filtrate lyophilized to give 2.6 g of the sodium salt of the title penicillin; $[\alpha]_D^{23} + 138°$ (cl, 75% dimethylformamide/pyridine).

$E_1^1$ 339 λ 317 nm pH 7.

EXAMPLE 2

N-[2-[4-(Acetylamino)phenyl]-4-hydroxy-5-pyrimidinylcarbonyl]amoxicillin

A mixture of 11.6 g (50 mmol) of 2-(4-aminophenyl)-4-hydroxy-5-pyrimidine carboxylic acid, 200 ml glacial acetic acid, and 10.5 ml (110 mmol) of acetic anhydride is heated at reflux for 4 hrs. The mixture is cooled, filtered, and the solid washed with ether and dried under vacuum at 50° to give 13.3 g of 2-[4-(acetylamino)phenyl]-4-hydroxy-5-pyrimidine carboxylic acid; mp>310°.

A mixture of 10.93 g (40 mmol) of the above pyrimidine acid, 165 ml of N,N-dimethylacetamide, and 9.73 g of carbonyldiimidazole is stirred at 50° for 1 hr and for an additional 3 hrs at room temperature. The solid is filtered, washed with tetrahydrofuran and ether, and dried under vacuum overnight to give 13.97 g of 2-[4-(acetylamino)phenyl]-4-hydroxy-5-pyrimidine carboxylic acid imidazolide.

A suspension 7.75 g (12.9 mmol) of amoxicillin dimethyl sulfoxide complex and 150 ml of N,N-dimethylacetamide is stirred at 0°-5° and 3.98 g (12.3 mmol) of the above imidazolide is added followed by 1.72 ml (12.3 mmol) of triethylamine. The resulting mixture is stirred overnight while warming to room temperature. The reaction is filtered and the filtrate poured into ice water. The pH is adjusted to 2 with hydrochloric acid and the precipitated solid filtered, washed with water, and suspended in 150 ml of water. The solid is dissolved as the pH is raised to 4.5 with 0.2 N sodium hydroxide with ice cooling. The solution is clarified by filtration and the filtrate lyophilized to give 5.7 g of the sodium salt of the title penicillin; $[\alpha]_D^{23} + 154°$ (c1, 75% dimethylformamide/pyridine).

$E_1^1$ 341 λ 316 nm pH 7.

EXAMPLE 3

N-[2-[4-(Trifluoroacetylamino)phenyl]-4-hydroxy-5-pyrimidinylcarbonyl]amoxicillin Using the method for the preparation of the side chain acid in Example 1, 13.86 g (60 mmol) of 2-(4-aminophenyl)-4-hydroxy-5-pyrimidine carboxylic acid, 25.2 ml (180 mmol) of triethylamine, 24 ml (190 mmol) of chlorotrimethylsilane, 600 ml of dichloromethane, and 9.3 ml (66 mmol) of trifluoroacetic anhydride gives 19.2 g of 2-[4-(trifluoroacetylamino)phenyl]-4-hydroxy-5-pyrimidine carboxylic acid; mp 293°-295° dec.

A mixture of 17.0 g (52 mmol) of the above pyrimidine acid, 16.85 g (104 mmol) of carbonyldiimidazole, and 170 ml tetrahydrofuran is stirred at 44°-50° for 35 min and at room temperature for 2 hrs. The solid is filtered, washed with tetrahydrofuran and ether, and dried overnight at 45° under reduced pressure to give 13.9 g of 2-[4-(trifluoroacetylamino)phenyl]-4-hydroxy-5-pyrimidine carboxylic acid imidazolide.

A 60 ml portion of N,N-dimethylacetamide is stirred at 0°-5° and 12.52 g (21 mmol) of amoxicillin dimethyl sulfoxide complex, 7.54 g (20 mmol) of the above imidazolide, and 2.8 ml (20 mmol) of triethylamine are added. The ice bath is removed and the reaction mixture stirred at room temperature for 2 hrs. The solution is poured into 300 ml of ice and water containing 20 ml 1 N hydrochloric acid. The pH is adjusted to 2.5 with 1 N hydrochloric acid and the solid filtered. The solid is twice suspended in 300 ml water, stirred and filtered. Finally the solid is suspended in 200 ml of water cooled in ice and the pH adjusted to 6.1 with 0.2 N and 1 N sodium hydroxide. Insolubles are removed by filtration and the filtrate lyophilized to give 12.1 g of the sodium salt of the title penicillin; $[\alpha]_D^{23} + 147°$ (c1, 75% dimethylformamide/pyridine).

$E_1^1$ 324 λ 315 nm pH 7
242 280

EXAMPLE 4

N-[2-[4-(Cyanoacetylamino)phenyl]-4-hydroxy-5-pyrimidinylcarbonyl]amoxicillin

Using the method for the preparation of the side chain acid in Example 1, 9.2 g (40 mmol) of 2-(4-aminophenyl)-4-hydroxy-5-pyrimidine carboxylic acid, 16.8 ml (120 mmol) of triethylamine, 16 ml (126 mmol) of chlorotrimethylsilane, 400 ml of dichloromethane, and 5.0 (45 mmol) of cyanoacetyl chloride [Org. Syn. Col. Vol. V, p. 171] gives 12.3 g of 2-[4-(cyanoacetylamino)phenyl]-4-hydroxy-5-pyrimidine carboxylic acid as the monohydrate; mp>280°.

A solution of 7.5 g (25 mmol) of the above pyrimidine acid and 80 ml of N,N-dimethylacetamide is stirred at 0°-5° and 3.2 g (28 mmol) of N-hydroxysuccinimide is added followed by dropwise addition of a solution of 5.8 (28 mmol) of dicyclohexylcarbodiimide and 20 ml of N,N-dimethylacetamide during a 20 min period. The ice bath is removed and the mixture stirred at room temperature for 4 hrs and another 1.2 g (12 mmol) of N-hydroxysuccinimide and a solution of 2.1 g (12 mmol) of dicyclohexylcarbodiimide and N,N-dimethylacetamide is added. The mixture is stirred overnight at room temperature and filtered. The filtrate is evaporated under high vacuum and the residue treated with 400 ml of tetrahydrofuran. The solid is filtered, washed with ether, and dried to give 4.4 g of 2-[4-(cyanoacetylamino)phenyl]-4-hydroxy-5-pyrimidine carboxylic acid N-hydroxysuccinimide ester.

A solution of 2.1 g (4.4 mmol) of amoxicillin dimethyl sulfoxide complex, 1.6 g (4 mmol) of the above N-hydroxysuccinimide ester, and 30 ml of N,N-dimethylacetamide is stirred at 0°-5° for 5 min. The ice bath is removed and stirring is continued for 3 hrs at room temperature. The solution is refrigerated for 1 hr and treated with 1.5 ml (4.95 mmol) of 3.3 M sodium 2-ethyl hexanoate in N,N-dimethylacetamide. The resulting solution is added slowly with stirring to 400 ml of ice cooled ethyl acetate. The precipitate is filtered, washed with ether, and dissolved in water. The pH is taken to 2.5 with 1 N hydrochloric acid and the solid filtered. The solid is suspended in water, filtered, and resuspended in 100 ml water and the pH adjusted to 6.0 with 1 N sodium hydroxide. The clear solution is lyophilized to give 1.95 g of the sodium salt of the title penicillin; $[\alpha]_D^{23} + 126°$ (c1, pH 7).

$E_1^1$ 328 λ 317 nm pH 7.

EXAMPLE 5

N-[2-[4-(Methoxyacetylamino)phenyl]-4-hydroxy-5-pyrimidinylcarbonyl]ampicillin

A suspension of 6.9 g (30 mmol) of 2-(4-aminophenyl)-4-hydroxy-5-pyrimidine carboxylic acid and 400 ml of dichloromethane is stirred at room temperature and 16.6 ml (120 mmol) of triethylamine is added followed by 11.3 ml (90 mmol) of chlorotrimethylsilane. The mixture is stirred at room temperature for 30 min and 3.2 ml (30 mmol) of methoxyacetyl chloride in 10 ml of dichloromethane is added dropwise at 0°. The resulting mixture is stirred for 18 hrs at room temperature and 15 ml of water and 50 ml of methanol are added. The solid is filtered, washed, and dried to give 8.2 g of 2-[4-(methoxyacetylamino)phenyl]-4-hydroxy-5-pyrimidine carboxylic acid. An additional 3.2 g is obtained by evaporation of the filtrate. After recrystallization from dimethyl sulfoxide-water, the material has mp 297°-300° dec.

A mixture of 3.03 g (10 mmol) of the above pyrimidine acid 3.2 g (20 mmol) of carbonyldiimidazole, and 40 ml of dimethylformamide is stirred at 50° for 1 hr and at room temperature for 2 hrs. The reaction is diluted with 50 ml of ether and the solid filtered, washed with acetonitrile and ether, and dried to give 2.94 g of 2-[4-(methoxyacetylamino)phenyl]-4-hydroxy-5-pyrimidine carboxylic acid imidazolide.

A suspension of 4.05 g (9 mmol) of ampicillin triethylamine salt and 25 ml of dry dimethylformamide is stirred at room temperature and 2.83 g (8 mmol) of the above imidazolide is added. The reaction is stirred at room temperature for 1 hr and the solution is poured into ether. The precipitated solid is filtered and dissolved in 100 ml of cold water. The pH is lowered to 2.5 with hydrochloric acid. The resulting solid is filtered, suspended in 200 ml of cold water, and dissolved by adjusting the pH to 6.5 with aqueous sodium hydroxide. The solution is clarified by filtration and the filtrate lyophilized to give 5.0 g of the title penicillin as the sodium salt; $[\alpha]_D^{25} + 135°$ (c1, methanol).

$E_1^1 328 \lambda 316$ nm pH 7.

EXAMPLE 6

N-[2-[4-[(2-Ethoxy-1,2-dioxoethyl)amino]phenyl]-4-hydroxy-5-pyrimidinylcarbonyl]amoxicillin A suspension of 5.08 g (22 mmol) of 2-(4-aminophenyl)-4-hydroxy-5-pyrimidine carboxylic acid and 210 ml of dichloromethane is stirred at room temperature and 8.25 ml (66 mmol) of chlorotrimethylsilane is added followed by 9.24 ml (66 mmol) of triethylamine. The solution is stirred at room temperature for 10 min, cooled to 0°-5°, and 3.43 ml (44 mmol) of ethyl oxalyl chloride is added followed by 6.16 ml (44 mmol) of triethylamine. The reaction mixture is stirred at room temperature for 45 min and filtered. The filtrate is evaporated and the residue treated with ice water. The solid is filtered, washed with ethanol and ether, and dried to afford 6.8 g of 2-[4-[(2-ethoxy-1,2-dioxoethyl)amino]phenyl]-4-hydroxy-5-pyrimidine carboxylic acid.

A mixture of 5.96 g (18 mmol) of the above pyrimidine acid, 4.37 g (27 mmol) of carbonyldiimidazole, and 90 ml of dimethylformamide is stirred at 60° for 10 min and at room temperature for 1.5 hrs. The reaction mixture is diluted with 100 ml of ether and the solid filtered, washed with ether, and dried to give 2.52 g of 2-[4-[(2-ethoxy-1,2-dioxoethyl)amino]phenyl]-4-hydroxy-5-pyrimidine carboxylic acid imidazolide. The filtrate is treated with 150 ml of ether and another 1.32 g of imidazolide is obtained.

A suspension of 8.5 g (14 mmol) of amoxicillin dimethyl sulfoxide complex and 30 ml of dimethyl sulfoxide is stirred at 0°-5° and 2 ml (14 mmol) of triethylamine is added followed by 5.4 g (14 mmol) of the above imidazolide. After stirring 2.5 hrs at room temperature, the clear mixture is poured into 500 ml of ether. The supernatant is decanted from the gum and the residue washed with ether. The residue is dissolved in 50 ml of water and the pH is adjusted to 2.9 with hydrochloric acid. The precipitate is filtered, washed with water, and suspended in 100 ml of ice water. The pH is raised to 6.7 with aqueous sodium hydroxide and the filtered solution lyophilized to give 9.7 g of the sodium salt of the title penicillin; $[\alpha]_D^{25} + 119°$ (c1, pH 7).

$E_1^1 348 \lambda 321$ nm pH 7.

EXAMPLE 7

N-[2-[4-[(2,2,2-Trifluoroethyl)thio]acetylamino]-phenyl]-4-hydroxy-5-pyrimidinylcarbonyl]amoxicillin Using the method for the preparation of the side chain acid in Example 1, 4.62 g (20 mmol) of 2-(4-aminophenyl)-4-hydroxy-5-pyrimidine carboxylic acid, 8.4 ml (60 mmol) of triethylamine, 8.0 ml (63 mmol) of chlorotrimethylsilane, 200 ml of dichloromethane, and 4.33 g (22 mmol) of 2-(2,2,2-trifluoroethyl)thio]acetyl chloride [J. Med. Chem., 20, 30(1977)] gives 7.4 g of [2-[4-[(2,2,2-trifluoroethyl)thio]acetylamino]phenyl]-4-hydroxy-5-pyrimidine carboxylic acid; mp >300° dec.

A suspension of 3.87 g (10 mmol) of the above pyrimidine acid and 25 ml of N,N-dimethylacetamide is stirred at about 40° and 3.24 (20 mmol) of carbonyldiimidazole is added. The reaction mixture is stirred at room temperature for 2.5 hrs and the solution concentrated under high vacuum. The heavy oil is added dropwise to 100 ml of rapidly stirred ethyl acetate. The solid is filtered, washed with ethyl acetate and dried under vacuum to give 4.00 g of 2-[4-[(2,2,2-trifluoroethyl)thio]acetylamino]phenyl-4-hydroxy-5-pyrimidine carboxylic acid imidazolide.

A solution 1.75 g (4 mmol) of the above imidazolide and 15 ml of N,N-dimethylacetamide is stirred at room temperature and 2.65 g (4 mmol) of amoxicillin dimethyl sulfoxide complex is added. The solution is stirred for 3 hrs at room temperature and 1.2 ml (3.96 mmol) of 3.3 M sodium 2-ethylhexanoate in N,N-dimethylacetamide is added. The resulting solution is slowly added to 200 ml of ethyl acetate with rapid stirring. The precipitate is filtered, washed with ethyl acetate, and dried under vacuum to give 3.00 g of product. The solid is dissolved in 100 ml water and filtered. The pH is adjusted to pH 2.5 with 1 N hydrochloric acid. The precipitate is filtered, washed with ice water, resuspended in 75 ml of water, and the pH adjusted to 6.5 with 1 N sodium hydroxide. The solution is lyophilized to give 2.5 g of the sodium salt of the title penicillin; $[\alpha]_D^{23} + 133°$ (c1, 75% dimethylformamide/pyridine).

| $E_1^1$ | 327 | $\lambda$ | 358 | nm | pH 7 |
|---|---|---|---|---|---|
| | 127 | | 271 | | |

EXAMPLE 8

N-[2-[4-(N-Ethylcarbamoylamino)phenyl]-4-hydroxy-5-pyrimidinylcarbonyl]amoxicillin A suspension of 4.6 g (20 mmol) of 2-(4-aminophenyl)-4-hydroxy-5-pyrimidine carboxylic acid, 2.36 ml (30 mmol) of ethyl isocyanate, and 70 ml of dimethylformamide is stirred at room temperature and 2.8 ml (20 mmol) of triethylamine is added. The resulting solution is allowed to stand overnight at room temperature and another 2.36 ml (20 mmol) of ethyl isocyanate is added. After 6 hrs the dimethylformamide is evaporated under high vacuum and the residue is treated with 100 ml of water. The solid is filtered and dried to give 1.5 g of 2-[4-(N-ethylcarbamoylamino)phenyl]-4-hydroxy-5-pyrimidine carboxylic acid. The filtrate is acidified to pH 2.5 with hydrochloric acid and another 3.10 g of acid is obtained.

A suspension of 4.6 g (15.2 mmol) of the above pyrimidine acid and 25 ml of N,N-dimethylacetamide is stirred at 0°-5° and 4.9 g (30 mmol) of carbonyldiimidazole is added. The mixture is stirred for 2 hrs as the ice bath melts and another 2.5 g (15 mmol) of carbonyldiimidazole is added. Stirring is continued for 2 hrs and 50 ml of tetrahydrofuran is added and the reaction is refrigerated overnight. A 200 ml portion of ether is added and the precipitated solid is filtered, washed with ether, and dried under high vacuum over phosphorus pentoxide to give 5.9 g of 2-[4-(N-ethylcarbamoylamino)phenyl]-4-hydroxy-5-pyrimidine carboxylic acid imidazolide.

A mixture of 7.6 g (11 mmol) of amoxicillin dimethyl sulfoxide complex, 3.5 g (10 mmol) of the above imidazolide, and 50 ml of N,N-dimethylacetamide is stirred at 0°–5° and 1.4 ml (10 mmol) of triethylamine is added. The reaction is stirred for 4 hrs as the ice bath melts and 3 ml (10 mmol) of 3.3 M sodium 2-ethylhexanoate in N,N-dimethylacetamide is added. The solution is added dropwise to 800 ml of stirring ethyl acetate. The precipitated solid is filtered, washed with ether, and dissolved in 200 ml of water. The pH is adjusted to 2.5 with 1 N hydrochloric acid and the solid filtered, suspended in water, filtered, and resuspended in 100 ml of cold water. The pH is adjusted to 6.5 with 1 N sodium hydroxide and the solution clarified by filtration. The filtrate is lyophilized to give 5.2 g of the title penicillin as the sodium salt; $[\alpha]_D^{23} + 100$ (cl, pH 7). $E_1^1 386 \lambda 325$ nm pH 7.

STARTING MATERIAL 2-(4-Aminophenyl)-4-hydroxy-5-pyrimidine carboxylic acid

A solution of 14.8 g (0.641 mmol) of sodium in 750 ml of dry ethanol is stirred at 0° and 44.6 g (0.214 mmol) of 4-aminobenzamidine.2HCl [Shaw and Cooley, J. Am. Chem. Soc., 79, 3561 (1957)] is added. The mixture is stirred 5 min under nitrogen and 46.2 g (0.214 mmol) of diethyl ethoxymethylenemalonate is added. After stirring for 30 min, the mixture is refluxed for 4 hrs and allowed to stand overnight at room temperature. The salt is filtered and washed with isopropanol. The salt is suspended in 214 ml of 2 N potassium hydroxide and stirred at 70° for 4 hr. After treating with a small amount of charcoal, the filtrate is added to 325 ml of 2 N hydrochloric acid with stirring. The acid is filtered, washed with water, ethanol, and ether, and dried to give 50.8 g of the title compound, mp 312°–314° dec. The product is recrystallized from N,-N-dimethylacetamide-water to give 44.5 g mp 313°–314° dec.

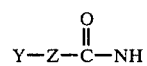

We claim:

1. A compound of the formula

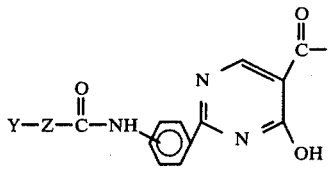

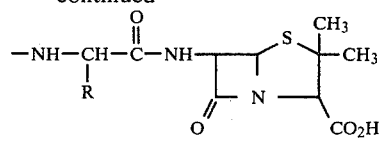

and pharmaceutically acceptable salts thereof; wherein Z is a single bond and Y is lower alkyl, dichloromethyl, benzyl, $CF_3$, lower alkyl amino, lower alkyl carbonyl, lower alkoxy carbonyl, benzyloxy, and lower alkoxy, where Z is a methylene group and Y is cyano, lower alkoxy, tetrazolyl, or $R^1 CH_2S$ where $R^1$ is $CF_3$ or CN and R is phenyl, 4-hydroxyphenyl, 2-thienyl or cyaclohexa-1,4-dien-1-yl.

2. The compounds of claim 1 wherein $$Y-Z-\overset{O}{\underset{\|}{C}}-NH$$

is in the p position and R is phenyl or 4-hydroxyphenyl.

3. A compound of claim 1 having the name N-[2-[4-(Dichloroacetylamino)phenyl]-4-hydroxy-5-pyrimidinylcarbonyl]amoxicillin and pharmaceutically acceptable salts thereof.

4. A compound of claim 1 having the name N-[2-[4-(Acetylamino)phenyl]-4-hydroxy-5-pyrimidinylcarbonyl]amoxicillin and pharmaceutically acceptable salts thereof.

5. A compound of claim 1 having the name N-[2-[4-(Trifluoroacetylamino)phenyl]-4-hydroxy-5-pyrimidinylcarbonyl]amoxicillin and pharmaceutically acceptable salts thereof.

6. A compound of claim 1 having the name N-[2-[4-(Cyanoacetylamino)phenyl]-4-hydroxy-5-pyrimidinylcarbonyl]amoxicillin and pharmaceutically acceptable salts thereof.

7. A compound of claim 1 having the name N-[2-[4-(Methoxyacetylamino)phenyl]-4-hydroxy-5-pyrimidinylcarbonyl]ampicillin and pharmaceutically acceptable salts thereof.

8. A compound of claim 1 having the name N-[2-[4-[(2-Ethoxy-1,2-dioxoethyl)amino]phenyl]-4-hydroxy-5-pyrimidinylcarbonyl]amoxicillin and pharmaceutically acceptable salts thereof.

9. A compound of claim 1 having the name N-[2-[4-[(2,2,2-Trifluoroethyl)thio]acetylamino]phenyl]-4-hydroxy-5-pyrimidinylcarbonyl]amoxicillin and pharmaceutically acceptable salts thereof.

10. A compound of claim 1 having the name N-[2-[4-(N-Ethylcarbamoylamino)phenyl]-4-hydroxy-5-pyrimidinylcarbonyl]amoxicillin and pharmaceutically acceptable salts thereof.

11. An antibacterial pharmaceutical composition comprising from 50 mg to 1000 mg of a compound of claim 1 and a pharmaceutical carrier.

12. A method for treating bacterial infections which comprises administering 5 mg to 100 mg per kg to an infected mammal of the pharmaceutical composition of claim 11.

* * * * *